(12) United States Patent
Stamler

(10) Patent No.: US 7,045,152 B2
(45) Date of Patent: *May 16, 2006

(54) TREATING PULMONARY DISORDERS WITH GASEOUS AGENT CAUSING REPLETION OF GSNO

(75) Inventor: Jonathan S. Stamler, Chapel Hill, NC (US)

(73) Assignee: Duke University, Durham, NC (US)

( * ) Notice: Subject to any disclaimer, the term of this patent is extended or adjusted under 35 U.S.C. 154(b) by 352 days.

This patent is subject to a terminal disclaimer.

(21) Appl. No.: 09/782,077

(22) Filed: Feb. 14, 2001

(65) Prior Publication Data

US 2001/0012834 A1 Aug. 9, 2001

Related U.S. Application Data

(63) Continuation-in-part of application No. 09/390,215, filed on Sep. 8, 1999, now Pat. No. 6,314,956.

(51) Int. Cl.
| | |
|---|---|
| *A61K 9/72* | (2006.01) |
| *A61K 31/198* | (2006.01) |
| *A61K 31/375* | (2006.01) |
| *A61K 33/00* | (2006.01) |
| *A61K 45/00* | (2006.01) |
| *A61P 11/00* | (2006.01) |
| *A61P 11/06* | (2006.01) |
| *A61P 9/00* | (2006.01) |

(52) U.S. Cl. ............... 424/718; 424/600; 424/607; 424/703; 424/708; 424/709; 424/711; 424/713; 514/474; 514/561; 514/562; 514/563; 514/645; 514/663; 514/708; 514/709; 514/711; 514/740; 514/771; 514/826; 514/851; 514/929; 514/958; 514/959

(58) Field of Classification Search ............ 424/600, 424/708, 718, 673, 703, 706, 711, 712, 713, 424/722, 723, 607, 709; 514/663, 826, 851, 514/929, 474, 506, 509, 561–563, 579, 644, 514/645, 708, 888, 959; 128/200.24; 604/23

See application file for complete search history.

(56) References Cited

U.S. PATENT DOCUMENTS

| | | | |
|---|---|---|---|
| 4,353,843 A | 10/1982 | Doumaux, Jr. et al. ...... 260/466 |
| 4,908,466 A | 3/1990 | Nelson ....................... 558/488 |
| 5,278,192 A | 1/1994 | Fung et al. ................. 514/645 |
| 5,412,147 A | 5/1995 | Landscheidt et al. ....... 558/488 |
| 5,485,827 A | 1/1996 | Zapol et al. ............ 128/200.14 |
| 5,489,610 A | 2/1996 | Fung et al. ................. 514/506 |
| 5,570,683 A * | 11/1996 | Zapol ..................... 128/200.14 |
| 5,571,524 A | 11/1996 | Kitakaze et al. ............. 424/423 |
| 5,583,101 A | 12/1996 | Stamler et al. ............. 424/718 |
| 5,649,322 A | 7/1997 | Landscheidt et al. ....... 558/488 |
| 5,713,349 A | 2/1998 | Keaney ................. 128/204.23 |
| 5,770,645 A | 6/1998 | Stamler et al. ............. 524/419 |
| 5,823,180 A | 10/1998 | Zapol ..................... 128/200.24 |
| 5,824,669 A | 10/1998 | Garvey et al. .............. 514/174 |
| 5,863,890 A | 1/1999 | Stamler et al. ................. 514/2 |
| 5,958,427 A | 9/1999 | Salzman et al. ............. 424/400 |
| 6,314,956 B1 * | 11/2001 | Stamler et al. ......... 128/200.24 |
| 6,945,247 B1 * | 9/2005 | Stamler et al. ......... 128/200.14 |

OTHER PUBLICATIONS

Embase abstract, accession No. 20000083448 (2000).*
Chemical Abstracts 115:56107 (1991).*
Medline abstract, accession No. 92296647 (1992).*
File Toxcenter, STN Online, Accession No. 2002:618658, abstracting Environmental Health Criteria, 1991, vol. 19, p. 1-48.*

* cited by examiner

*Primary Examiner*—John Pak
(74) *Attorney, Agent, or Firm*—Mintz, Levin, Cohn, Ferris, Glovsky and Popeo, P.C.; Ivor R. Elrifi; Matthew Pavao

(57) ABSTRACT

Pulmonary disorders in which the GSNO pool or glutathione pool in the lung is depleted and where reactive oxygen species in lung are increased, are treated by delivering into the lung as a gas, agent causing repletion or increase of the GSNO pool or protection against toxicity and does so independently of reaction with oxygen. Agents include ethyl nitrite, NOCl, NOBr, NOF, NOCN, $N_2O_3$, HNO, and $H_2S$. Optionally, N-acetylcysteine, ascorbate, $H_2S$ or HNO is administered in addition to other GSNO repleting agent to potentiate the effect of said agent.

18 Claims, 1 Drawing Sheet

TREATING PULMONARY DISORDERS WITH GASEOUS AGENT CAUSING REPLETION OF GSNO

CROSS-REFERENCE TO RELATED APPLICATION

This application is a continuation-in-part of U.S. application Ser. No. 09/390,215, filed on Sep. 8, 1999, now U.S. Pat. No. 6,314,956.

TECHNICAL FIELD

This invention relates to treating lung disorders by delivery of a gas into the lungs.

BACKGROUND OF THE INVENTION

Inhaled nitric oxide (NO) is used to treat elevated pulmonary pressures and pulmonary disorders associated with hypoxemia. This provides hypoxemia relieving and smooth muscle constriction relieving effects, but side effects include inflammation, airway hyperactivity, hemorrhage, and reaction with hemoglobin resulting in interference with its oxygen delivery function. In addition, this impairs renal function and even increases mortality in some subsets. The hypoxemia relieving and smooth muscle constriction relieving effects are due mainly to the vasodilating effect of NO as NO does not mediate production of S-nitrosoglutathione in the lung effectively, as it requires reaction with oxygen for this purpose and this reaction does not proceed readily in the lung. On the other hand, the toxicity of NO is related to reactions with oxygen and reactive oxygen species and is mitigated by airway glutathione and thiols.

Use of nitric oxide-releasing compounds inhaled as solids or liquids in an aerosol (nebulized NO donor compounds) to treat pulmonary vasconstriction and asthma is described in Zapol U.S. Pat. No. 5,823,180. This method while offering certain advantages compared to NO administration has the disadvantages compared to inhaled NO administration that the distribution in the lungs is not matched to perfusion so NO deposits in places where it does not reach the blood and that the method is not readily carried out by an anesthesiologist since anesthesiologists do not normally administer liquids or powders. In addition, the pharmacokinetics of these compounds are different and may reveal systemic effects. Moreover, all the potential toxicities of inhaled NO gas are manifest also with nebulized NO donor compounds as these are converted to NO in the lung. The disadvantages of administering nebulized NO donor are indicated to be meaningful by the fact that inhaled gaseous NO is approved for use over inhaled liquid or inhaled solid NO-releasing compound.

The method of parent patent application Ser. No. 09/390,215 constitutes an improvement over the methods described above which rely on inhaled NO or nebulized NO donor. The method of Ser. No. 09/390,215 comprises delivery into the lungs of a patient with a pulmonary disorder associated with hypoxemia and/or smooth muscle constriction, as a gas, a therapeutically effective amount of a compound having an NO group and having a hypoxemia relieving and smooth muscle constriction relieving effect with said NO group being bound in said compound so that it does not form $NO_2$ or $NO_x$ (where $NO_x$ means NO, $N_2O_3$, $N_2O_4$, $OONO^-$, OONO• and any products of their reaction with NO or $NO_2$). This method provides the advantages of administering inhaled NO compared to administering nebulized NO donor, without the toxicities associated with NO inhalation. Other desired effects include reactions with thiols of the red blood cell rather than hemes of hemoglobin so as to improve systemic delivery of oxygen. The preferred treating agent for the method of Ser. No. 09/390,215 is ethyl nitrite.

SUMMARY OF THE INVENTION

This invention relies on the conception that for lung disorders associated with depletion of the S-nitrosoglutathione (GSNO) pool in lung or depletion of the glutathione pool in lung or increased production of reactive oxygen species in lung, treatment with inhaled gases to replete or increase the S-nitrosoglutathione pool and/or to react preferentially with glutathione to form other NO glutathione derivatives independently of reaction with oxygen, would provide the benefits of treatment using gas inhalation of matching ventilation to perfusion and suitability for administration by an anesthesiologist and the benefits of treatment using inhaled NO of hypoxemia relieving effect and/or smooth muscle relieving effect, and additionally would provide antimicrobial effect and anti-inflammatory activity, and these activities would be provided with less toxicities than previous alternative therapies. The totality of the benefits is important, for example, not only in respect to treatment of asthma, for example, which is associated with smooth muscle constriction in lung and can be associated with hypoxemia, and where lung infection can be a secondary problem, but also in respect to cystic fibrosis where airway lining can be impaired to the extent that relaxing of the airway is not therapeutic, but where antimicrobial effect is important to treat infection associated with cystic fibrosis or where increased GSNO or glutathione (GSH) reactive compounds can upregulate the cystic fibrosis transmembrane regulator. In respect to treating cystic fibrosis, inhaled gaseous GSNO repleting or increase causing agents also function better than inhaled NO because they cause increase in cystic fibrosis transmembrane regulator and inhaled NO does not and/or are less toxic than NO.

While it is known to treat lung disorders by inhibiting reduction of GSNO by administering inhibitor of S-nitrosoglutathione reductase, also known as glutathione dependent formaldehyde dehydrogenase (U.S. application Ser. No. 09/757,610, filed Jan. 11, 2001), and by preventing and/or accommodating for S-nitrosothiol breakdown by administering certain treating agents (U.S. application Ser. No. 09/403,775, filed Nov. 4, 1999), these patent applications do not specifically disclose delivery into the lungs as a gas, an agent which causes repletion or increase of the GSNO pool, and they do not consider thiols and other anti-oxidants such as N-acetylcysteine, ascorbate and $H_2S$ which can increase the GSNO pool.

The invention herein is directed to a method for treating a pulmonary disorder associated with depletion of the S-nitrosoglutathione pool in the lung or depletion of the glutathione pool in the lung or production of reactive oxygen species in the lung, in a patient having such disorder, which comprises delivery into the lungs of said patient as a gas, a therapeutically effective amount of an agent which causes repletion or increase of the S-nitrosoglutathione pool in the lung or protects against toxicity (as manifested by inflammation or fibrosis in lung or airway constriction or blood vessel constriction in lung or by ventilation perfusion mismatching in lung) where glutathione is depleted in lung (and/or is being oxidized by reactive oxygen species and thereby inactivated) or where reactive oxygen species are increased in the lung and does so independently of reaction with oxygen. As indicated above, inhaled NO does not replete or increase the S-nitrosoglutathione pool effectively but comparison of effect is not necessary since the language "independently of reaction with oxygen" excludes the administration of inhaled NO.

Above, matching ventilation to perfusion is mentioned. This means that blood vessels in lung are matched to air sacs of lung (alveoli). If a dilated blood vessel in lung is not juxtaposed to an air sac, oxygenation can be impaired by the dilation, and improved oxygen delivery to the air sac will not improve blood oxygenation. Matching ventilation to perfusion happens distinct from dilation of blood vessels in lung. This is explified in treatment by the administration of the vasorelaxant dobutamine, which, while dilating blood vessels in lung, impairs ventilation to perfusion matching.

The term "depletion of the S-nitrosoglutathione pool" is used herein to mean low GSNO content compared to normal, i.e., a level of GSNO less than 90% of normal, as determined, for example, by chemiluminescence analysis of the airway lining fluid.

The term "depletion of the glutathione pool" is used herein to mean less than 0.5 millimolar glutathione in airway lining fluid as determined, for example, by standard assays for low mass thiols and does not exclude the option of increasing glutathione or other thiol in airway lining fluid.

The term "increased production of reactive oxygen species in the lung" is used herein to mean any evidence of oxidant stress such as increased production of $H_2O_2$ in expired breath or increased bromotyrosine or nitrotyrosine formation, compared to normal, as determined, for example, by immunolabeling or other standard techniques.

The term "replete or increase the S-nitrosoglutathione pool" is used herein to mean preventing breakdown of GSNO, for example, by scavenging reactive oxygen species, or increasing levels of GSNO by molecules that generate either GSNO directly or GSNO like species which can be readily converted to GSNO including GSNO˙, GSNHOH or $GSNO_2$. The obtaining of this result can be determined, for example, by chemiluminescence analysis of airway lining fluid or exhaled breath.

The term "independently of reaction with oxygen" as used herein, means a direct reaction between delivered compound and glutathione in the physiological setting.

We turn now to optional additional treatments.

In one such case, N-acetylcysteine is administered to the patient in addition to the delivery into the lungs of the patient as a gas of the S-nitrosoglutathione pool repleting or increase causing agent, to mediate repletion or increase of the S-nitrosoglutathione pool and/or potentiate the effect of said S-nitrosoglutathione pool repleting or increasing agent administered as a gas; in another such case, alternative thiol repleting or increasing agents, such as pro-cysteine, are used. Administration of the N-acetylcysteine or alternative thiol repleting or increasing agent is in an amount effective to mediate repletion or increase of the S-nitrosoglutathione pool and/or potentiate the NO donor gas effect, in the lung. See Example VII and FIG. 1 for specifics of a treatment that was successful in the treatment of ARDS where all previous therapies failed.

In another such case, ascorbate is administered to the patient in addition to the delivery into the lungs of the patient as a gas of the S-nitrosoglutathione pool repleting or increase causing agent, to mediate repletion or increase of the S-nitrosoglutathione pool and/or potentiate the effect of said S-nitrosoglutathione pool repleting or increase causing agent administered as gas. Administration of the ascorbate is in an amount effective to mediate repletion or increase of the S-nitrosothiol pool in the lung and/or protect from injury as measured by indices such as decreased $H_2O_2$ in expired breadth or decreased thiobarbituric acid derivatives in expired breath or decreased carbon monoxide in expired breath or decreased nitration in lung.

If desired, both N-acetylcysteine and ascorbate can be administered to a patient in addition to delivery into the lungs of the patient as a gas of the S-nitrosoglutathione pool repleting or increase causing agent, to mediate repleting or increase of the S-nitrosoglutathione pool and/or potentiate the effect of said S-nitrosoglutathione pool repleting or increase causing agent administered as a gas.

In another case $H_2S$, and in still another case HNO or HNO donor compound, e.g., Angeli's salt or piloty acid, are given preferentially as gases, in the first case ($H_2S$) to replete glutathione and/or decrease reactive oxygen species and/or potentiate the effect of any other S-nitrosoglutathione pool repleting or increase causing agent administered, and in the second case (HNO or HNO donor compound) to raise GSNO levels in the lung, in addition to delivery into the lungs as a gas of other S-nitrosoglutathione pool repleting or increase causing agent.

DETAILED DESCRIPTION

Figure 1:
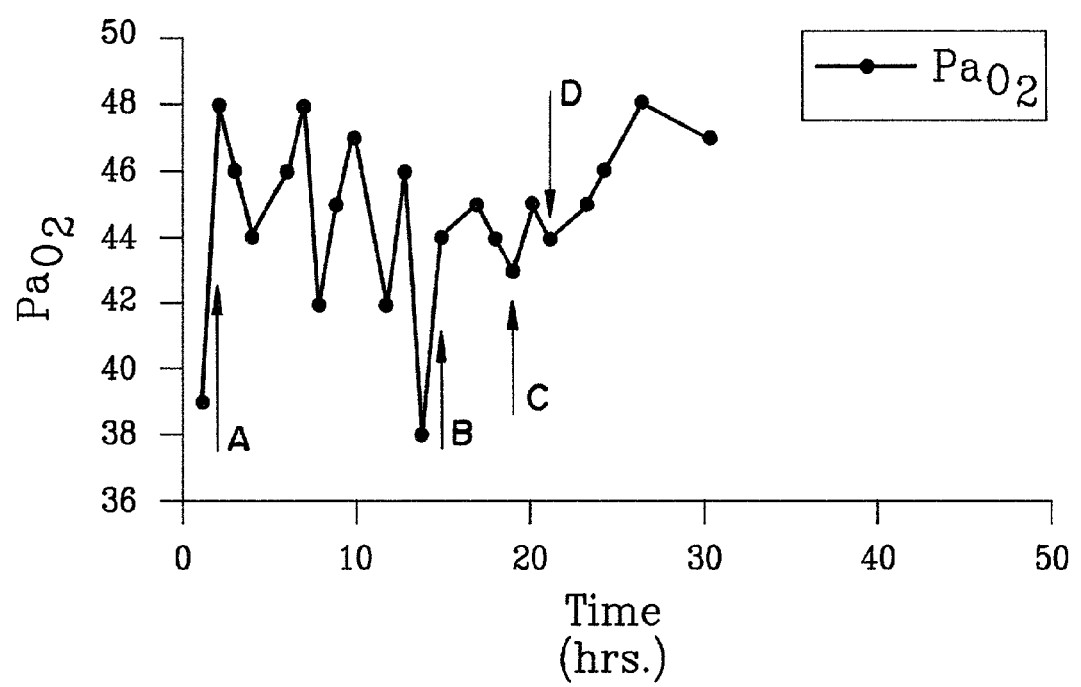
FIG. 1 is a graph of $Pa_{O2}$ versus time, and shows results of Example VII.

We turn now to the method herein for treating a pulmonary disorder associated with depletion of the S-nitrosoglutathione pool in the lung or depletion of the glutathione pool in the lung or production of reactive oxygen species in the lung in a patient having such disorder, which comprises delivery into the lungs of said patient as a gas, a therapeutically effective amount of an agent which causes repletion or increase of the S-nitrosoglutathione pool in the lung or protects against toxicity where glutathione is depleted in lung or where reactive oxygen species are increased in the lung and does so independently of reaction with oxygen (hereinafter sometimes referred to as GSNO repleting agent).

We turn now to the pulmonary disorders associated with depletion of the S-nitrosoglutathione pool in the lung or depletion of the glutathione pool in the lung or production of reactive oxygen species in the lung. These include pulmonary disorders associated with hypoxemia and/or smooth muscle constriction in the lungs and/or lung infection and/or lung injury. These disorders may include, for example, pulmonary hypertension, ARDS, asthma, pneumonia, pulmonary fibrosis/interstitial lung diseases, and cystic fibrosis. Pulmonary hypertension is associated with smooth muscle constriction in the lungs and can be associated with hypoxemia. ARDS is associated with hypoxemia and can be associated with smooth muscle constriction in the lung. Asthma is known to be associated with depletion of GSNO in lung and is associated with smooth muscle constriction in the lungs and can be associated with infection in the lungs and can be associated with hypoxemia. Cystic fibrosis is known to be associated with depletion of GSNO in lung and is associated with smooth muscle constriction in lungs and can be associated with infection in the lungs and can be associated with hypoxemia. Some cases of severe hypoxemia are associated with depletion of GSNO. Lung injury disorders associated with depletion of the S-nitrosoglutathione pool in the lung include, for example, subsets of persistent pulmonary hypertension of the newborn and asthma. Disorders associated with depletion of the glutathione pool in lung include ARDS, ventilation pneumonia and interstitial lung diseases. All of the above disorders are associated with production of reactive oxygen species in lung.

We turn now to the treating agents for the method herein, for delivery into the lungs as a gas, i.e., to the GSNO repleting agents for delivery into the lungs as a gas.

As indicated above, the limitation "independently of reaction with oxygen" excludes the administration of nitric oxide (NO).

There is overlap for the treating agents for administration as a gas for the method herein with the treating agents of Ser. No. 09/390,215 which are compounds capable of being administered as a gas, having an NO group and having a hypoxemia relieving and smooth muscle constriction relieving effect with said NO group being bound in said compound so it does not form $NO_2$ or $NO_x$ in the presence of oxygen or reactive oxygen species at body temperature where $NO_x$ is NO, $N_2O_3$, $N_2O_4$, OONO⁻, OONO• and any products of their interaction with NO or $NO_2$.

One GSNO repleting agent useful in the method herein for administration as a gas which is also the preferred treating agent in Ser. No. 09/390,215 is ethyl nitrite which is naturally a gas but is readily dissolved in ethanol to provide solution in liquid form for handing and is readily restored to gaseous form for administration as described below.

Other GSNO repleting agents useful in the method herein for administration as gases that are naturally gases, that is, have a boiling point at or below room temperature at atmospheric pressure, include methyl nitrite and trifluoronitrosomethane which are specifically mentioned as treating agents in Ser. No. 09/390,215.

Other GSNO repleting agents for use in the method herein which are naturally gases or which can be converted into a gas for administration which are not specifically mentioned in Ser. No. 09/390,215 but which meet the definition of compound to be administered in the method of Ser. No. 09/390,215 include NOX or XNO where X is halogen, e.g., Cl, Br or F, or hydrogen, or NOX or XNO generating agents, alkyl nitrososulfinates ($RSO_2NO$) where the alkyl group contains from 1 to 10 carbon atoms, thionitrosochloronitrite (SOClONO), thionyldinitrite ($SO(ONO)_2$) and alkyl thionitrites ($RSNO_2$) wherein the alkyl group contains from 1 to 10 carbon atoms, and nitrosourea.

GSNO repleting agents useful in the method herein for administration as gases which do not meet the definition of compound to be administered as a gas in Ser. No. 09/390, 215 are $N_2O_3$ (nitrogen trioxide) and $H_2S$. While these are normally considered toxic and strong irritants, they are pharmaceutically acceptable at the low concentrations used herein (0.1 to 100 ppm).

Other GSNO repleting agents useful in the method herein for administration as gases are compounds administrable as gases that prevent GSNO breakdown.

Dilution of the treating agents herein to 0.1 to 100 ppm for delivery into the lungs as a gas is typically appropriate.

Diluted treating agent is readily delivered into the lungs as a gas, using a ventilator which is a conventional device for administering gases into the lungs of a patient. A tube attached to the device passes the gas into the lungs at a rate and pressure consistent with maintaining a $Pa_{O2}$ of 90 mm Hg. Time periods of administration typically range from 1 minute to two or more days, and administration is suitably carried out until symptoms abate. Administration can also be carried out using a face mask.

The GSNO repleting agents useful in the method herein for administration as gases are readily delivered by dissolving them in solvent (e.g., ethanol in the case of ethyl nitrite) and bubbling $N_2$ or $O_2$ through a Milligan gas diffuser, e.g., at a flow rate ranging from 0.1 to 1 ml/min, e.g., at a flow rate of 0.5 ml/min, to produce $N_2$ or $O_2$ containing the GSNO repleting agent, and introducing this into the ventilation system for the patient by mixing output from the ventilator with $N_2$ or $O_2$ containing the GSNO repleting agent, e.g., to produce a concentration of 0.1 to 100 ppm treating agent in the resulting gas, and delivering this to the patient at a rate and pressure to maintain $Pa_{O2}$ at 90 mm Hg and/or GSNO concentration greater than 10 nanomolar in the airway lining. The concentration of GSNO repleting agent in the gas administered is proportional to the flow rate of $N_2$ or $O_2$ and the concentration of GSNO repleting agent in solvent.

As indicated above, a therapeutically effective amount is administered. In the case of hypoxemia, this is a hypoxemia relieving effective amount. In the case of smooth muscle constriction in lung, this is a smooth muscle constriction relieving effective amount. In the case of lung infection, this is an antimicrobial effective amount. In the case of lung injury, this is an anti-inflammatory and/or GSNO repleting effective amount. Administration is typically carried out for as long as symptoms ameliorate.

We turn now to the case where N-acetylcysteine is administered to the patient as a GSNO repleting agent and/or to potentiate the effect of other GSNO repleting agent, in addition to the delivery into the lungs of the patient as a gas of GSNO repleting agent. This is used in the same dosages and same routes of administration as it is now used for standard therapy to liquify secretions (e.g., in bronchitis), e.g., at a dosage ranging from 50 to 200 mg/kg with the preferred route of administration being intravenous or nebulized which dosage and route of administration are those indicated as used in combination with ethyl nitrite to treat hypertension to promote systemic release of NO from binding cysteine of hemoglobin in Ser. No. 09/390,215 and which combination and dosage and route of administration may also be used to treat angina.

We turn now to the case where ascorbate is administered to the patient as a GSNO repleting agent and/or to potentiate the effect of other GSNO repleting agent in addition to the delivery into the lungs of the patient as a gas of GSNO repleting agent. The ascorbate functions by scavenging free radicals that break down GSNO. The ascorbate can be any source of ascorbic acid, e.g., vitamin C or sodium ascorbate. The dose of the ascorbate is, for example, 0.5 to 2 grams every 6 hours, and is a free radical scavenging effective amount. The route of administration for the ascorbate is, for example, nebulized, intravenous or oral.

We turn now to the case where HNO is administered to the patient in non-gaseous or gaseous form in addition to the delivery into the lungs of the patient as a gas of other GSNO repleting agent. The dosage for HNO is, for example, 0.1 to 100 ppm in gaseous form (e.g., in nitrogen) or 1 μM to 100 mM (as Angeli's salt) in 3 cc of saline. The route of administration for HNO as a solution is by nebulizing in, for example, nitrogen gaseous carrier.

We turn now to the case where $H_2S$ is administered to the patient to replete or increase the S-nitrosoglutathione pool or to potentiate the effect of other GSNO repleting agent, in addition to the delivery into the lungs of the patient as a gas of other GSNO repleting agent. The dosage is 0.1 to 100 ppm, e.g., in nitrogen. The route of administration is, for example, via a ventilator.

The invention is illustrated in the following examples.

In the following examples, dilution with nitrogen and dilution with oxygen are typically interchangeable.

EXAMPLE I

A 63-year-old white male with primary pulmonary hypertension is treated with inhaled NOCl at 10 parts/million in nitrogen. Pulmonary systolic pressure drops from 40 to 30 mm Hg and the $PaO_2$ increases from 56 to 72 mm Hg.

EXAMPLE II

A 25-year-old white female with ARDS secondary to urosepsis is intubated with a $PaO_2$ of 14 mm Hg. She is given NOCN in nitrogen at 20 parts per million and the $PaO_2$ increases to 60.

EXAMPLE III

A 6-year-old boy presents in status asthmaticus. His $PO_2$ is 64 mm Hg and he is intubated. Efforts to ventilate are complicated by a pneumothorax. He is started on 20 ppm methylnitrososulfinate in nitrogen and airway pressures decrease.

EXAMPLE IV

A 17-year-old white male with cystic fibrosis presents with hypoxemia and pseudomonas pneumonia. A bronchoalveolar lavage (BAL) shows complete deficiency of GSNO. The patient is given inhaled thionitrosochloronitrite at 5 parts per million in nitrogen with repletion of GSNO. He is then converted to a nebulized solution (100 mM per 3 cc normal saline) which he is given every 6 hours for maintenance therapy. GSNO levels are sustained for four days and the infection resolves.

EXAMPLE V

A 46-year-old white female with sclerodoma and secondary pulmonary hypertension presents with a pulmonary pressure of 70 mm Hg and a $PO_2$ of 50 mm Hg. She is given inhaled thionyldinitrite of 20 ppm in nitrogen and pulmonary pressures fall to 60 mm Hg and the $PaO_2$ increases to 70 mm Hg.

EXAMPLE VI

A 60-year-old with acute myelogenous leukemia (AML) develops ARDS during induction chemotherapy. The $PO_2$ is 40 on 100% oxygen and the patient is intubated. Methylthionitrite is given at 20 parts per million oxygen with improvement in the $PaO_2$ to 70 mm Hg.

EXAMPLE VII

A 35-year-old female presented with acute viral pneumonia that progressed to ARDS. She failed all conventional therapy and became hemodynamically unstable. The $PaO_2$ on 100% oxygen was 39 mm Hg. Ethylnitrite (ENO) was started at 40 ppm in nitrogen with improvement in the $PaO_2$ to 48 mm Hg. The blood pressure stabilized. Over the following 12 hours the patient became progressively less responsive to ENO with the $PaO_2$ falling to 37 millimeters of mercury. The patient was then given nebulized N-acetylcysteine (cysteine), which immediately sensitized her to ENO and the $PaO_2$ rose to 46 mm Hg. ENO was stopped and the $PaO_2$ fell to 43 mm Hg. ENO in nitrogen was started again and the $PaO_2$ rose to 49 mm Hg. The results are shown in FIG. 1. Arrow A indicates response to initial ENO administration. Arrow B indicates response to ENO plus N-acetylcysteine administration. Arrow C indicates response to stopping ENO administration where $PaO_2$ fell to 43 mm Hg. Arrow D represents response to ENO administration after the response of arrow C.

EXAMPLE VIII

A 20-year-old white female with ARDS presents with a $PaO_2$ of 50 mm Hg. She is given inhaled ethylnitrite in nitrogen at 10 ppm for three days, at which time per $PaO_2$ falls to 40 mm Hg. Ascorbate is begun at 2 grams IV Q 6 hours and over the day her $PaO_2$ increases to 55 mm Hg.

EXAMPLE IX

A 15-year-old white female with cystic fibrosis presents with hypoxemia and pulmonary hemorrhage. A bronchoalveolar lavage reveals absence of GSNO and low levels of glutathione. She is begun on ethylnitrite at 20 parts per million in nitrogen, and N-acetylcysteine 50 mg/kg Q 6 hours and ascorbate IV 1 gram Q 6 hours. Over the following three days the hemorrhage stops and the patient reverts to her normal state of health. She is discharged on day 7.

EXAMPLE X

A 25-year-old white male presents to the emergency room with an asthmatic exacerbation. The forced expiratory volume in 1 second (FEV1) is 0.8 liters per minute. Following the standard bronchodilator regimen, the FEV1 increases to 1.5 liters per minute but breathing is still labored. GSNO levels in the airway lining are depleted. The patient is begun on $H_2S$ gas at 10 ppm in nitrogen and over the following day the FEV1 increases to 1.8 liters per minute. Ethyl nitrate is then started at 10 ppm in nitrogen and the FEV1 increases to 2 liters per minute.

EXAMPLE XI

A 17-year-old female with cystic fibrosis presents with labored breathing and increased sputum production. The she is begun on HNO 10 ppm in nitrogen with improvements in her symptomatic status. She is begun on Angeli's salt 100 mM in 3 cc normal saline nebulized Q 6 hours with decreases in sputum production over two days.

EXAMPLE XII

A 20-year-old with cystic fibrosis develops bronchospasm secondary to a severe pseudomonas infection. Analysis of bronchoalveolar lavage reveals an absence of GSNO. The patient is begun on ethylnitrite 10 parts per million in nitrogen and nebulized Angeli's salt (50 mM/3 cc normal saline). By day 2 the GSNO levels increase in the airway lining fluid and sputum production decreases. The patient's blood gases have improved.

Variations

Variations will be obvious to those skilled in the art. Thus, the scope of the invention is defined by the claims.

What is claimed is:

1. A method for treating a pulmonary disorder associated with depletion of the S-nitrosoglutathione pool in the lung or depletion of the glutathione pool in the lung or production of reactive oxygen species in the lung of a patient having such disorder which comprises delivering into the lungs of said patient as a gas, a therapeutically effective amount of an agent selected from the group consisting of: (a) compounds having an NO group and having a hypoxia relieving and smooth muscle constriction relieving effect with the said NO group being bound in said compound so it does not form $NO_2$, NO, $N_2O_3$, $N_2O_4$, $OONO^-$ and OONO• and any products of their interaction with NO or $NO_2$; and (b) $N_2O_3$; and (c) NOX, wherein X is halogen, hydrogen or CN, which causes repletion or increase of the S-nitrosoglutathione pool in the lung or protects against toxicity where glutathione is depleted in the lung or where reactive oxygen species are increased in the lung and does so independently of reaction with oxygen.

2. The method of claim 1 where the pulmonary disorder is associated with hypoxemia and/or smooth muscle constriction in the lungs and/or lung infection and/or lung injury.

3. The method of claim 1 where the agent is naturally a gas.

4. The method of claim 1 where the agent is NOX where X is halogen or hydrogen.

5. The method of claim 4 where the halogen is selected from the group consisting of chlorine and fluorine.

6. The method of claim 1 where N-acetylcysteine is also administered, the administration of the N-acetylcysteine being in an amount effective to mediate repletion or increase of the S-nitrosoglutathione pool or potentiate the effect of said agent, in the lung.

7. The method of claim 1 where ascorbate is also administered, the administration being of the ascorbate being in an amount effective to mediate repletion or increase of the S-nitrosoglutathione pool in the lung and/or protect the lung from injury.

8. The method of claim 1 where liquid HNO is also administered, the administration of HNO being in an amount effective to mediate repletion or increase of the S-nitrosoglutathione pool in the lung.

9. The method of claim 1 where the disorder is selected from the group consisting of pulmonary hypertension, primary pulmonary hypertension, secondary pulmonary hypertension, and persistent pulmonary hypertension of the newborn.

10. The method of claim 1 where the disorder is pneumonia or ventilation pneumonia.

11. The method claim 1 where the disorder is selected from the group consisting of interstitial lung diseases, pulmonary fibrosis, and cystic fibrosis.

12. The method of claim 1 where the disorder is asthma.

13. The method of claim 1 where the disorder is adult respiratory distress syndrome.

14. The method of claim 1 where the agent is HNO.

15. The method of claim 1 where the agent comprises NOCl or NOCN.

16. The method of claim 1 where the agent is a compound selected from the group consisting of methylnitrososulfinate, methylthionitrite, thionitrosochloronitrite, and thionyldinitrite.

17. The method of claim 1 where the agent is trifluoronitrosomethane or methylnitrite.

18. The method of claim 1 where the agent is ethylnitrite.

* * * * *